United States Patent
Gu et al.

(10) Patent No.: US 9,433,382 B2
(45) Date of Patent: Sep. 6, 2016

(54) USER INTERFACE SYSTEM AND OPTICAL FINGER MOUSE SYSTEM

(71) Applicant: PixArt Imaging Inc., Hsin-Chu County (TW)

(72) Inventors: Ren-Hau Gu, Hsin-Chu County (TW); Ming-Tsan Kao, Hsin-Chu County (TW); Sen-Huang Huang, Hsin-Chu County (TW)

(73) Assignee: PIXART IMAGING INC, Hsin-Chu County (TW)

( * ) Notice: Subject to any disclaimer, the term of this patent is extended or adjusted under 35 U.S.C. 154(b) by 126 days.

(21) Appl. No.: 13/632,327

(22) Filed: Oct. 1, 2012

(65) Prior Publication Data

US 2013/0127714 A1  May 23, 2013

(30) Foreign Application Priority Data

Nov. 22, 2011  (TW) .............................. 100142660 A (51) Int. Cl.
*A61B 5/00*  (2006.01)
*A61B 5/11*  (2006.01)
*A61B 5/1455*  (2006.01)
*G06F 3/03*  (2006.01)

(52) U.S. Cl.
CPC ........... *A61B 5/6898* (2013.01); *A61B 5/1128* (2013.01); *A61B 5/14552* (2013.01); *A61B 5/721* (2013.01); *G06F 3/0317* (2013.01); *G06F 2203/0338* (2013.01)

(58) Field of Classification Search
CPC ..... G06F 3/042; G06F 3/033; A61B 5/1455; A61B 5/14552; A61B 5/14532; A61B 5/0059; A61B 5/6826
USPC ......... 345/158, 175; 600/300–301, 309–310, 600/322
See application file for complete search history.

(56) References Cited

U.S. PATENT DOCUMENTS

| | | | |
|---|---|---|---|
| 6,650,318 B1 * | 11/2003 | Arnon ........................... | 345/168 |
| 7,072,701 B2 * | 7/2006 | Chen et al. .................... | 600/331 |
| 8,509,869 B2 * | 8/2013 | Baker et al. ................... | 600/323 |
| 8,512,240 B1 * | 8/2013 | Zuckerman-Stark .... | A61B 5/02 128/924 |
| 9,204,843 B2 * | 12/2015 | Gu ........................ | A61B 5/6886 |
| 2002/0024500 A1 * | 2/2002 | Howard ......................... | 345/158 |
| 2002/0038079 A1 * | 3/2002 | Steuer et al. .................. | 600/322 |
| 2003/0036685 A1 * | 2/2003 | Goodman ...................... | 600/300 |
| 2008/0091121 A1 * | 4/2008 | Sun et al. ...................... | 600/587 |
| 2008/0132770 A1 * | 6/2008 | Ayers et al. ................... | 600/323 |
| 2009/0015558 A1 | 1/2009 | Hung | |
| 2009/0093687 A1 * | 4/2009 | Telfort et al. .................. | 600/300 |
| 2009/0128489 A1 * | 5/2009 | Liberty et al. ................ | 345/158 |
| 2009/0299160 A1 * | 12/2009 | Moridaira ............ | A61B 5/1455 600/322 |
| 2010/0113900 A1 * | 5/2010 | Shakespeare et al. ........ | 600/316 |
| 2010/0123655 A1 | 5/2010 | Lai | |
| 2010/0324398 A1 * | 12/2010 | Tzyy-Ping ......... | A61B 5/14532 600/365 |
| 2011/0141016 A1 * | 6/2011 | Lu et al. ....................... | 345/163 |

(Continued)

*Primary Examiner* — Christopher E Leiby
(74) *Attorney, Agent, or Firm* — Hauptman Ham, LLP (57) ABSTRACT

There is provided a user interface system including a slave device and a master device. The slave device provides light of two different wavelengths to illuminate a finger surface, receives reflected light from the finger surface to generate a plurality of image frames, calculates and outputs an image data associated with a predetermined number of the image frames. The master device calculates a contact status and a displacement of the finger surface and a physiological characteristic of a user according to the image data.

17 Claims, 5 Drawing Sheets

(56) References Cited

U.S. PATENT DOCUMENTS

| | | | |
|---|---|---|---|
| 2011/0320216 A1* | 12/2011 | Kasmark | 705/2 |
| 2012/0004517 A1* | 1/2012 | Starr et al. | 600/301 |
| 2014/0200416 A1* | 7/2014 | Kashef | G06F 19/3418 600/301 |
| 2015/0099987 A1* | 4/2015 | Bhatkar | A61B 5/165 600/479 |

* cited by examiner

FIG. 7

USER INTERFACE SYSTEM AND OPTICAL FINGER MOUSE SYSTEM

CROSS REFERENCE TO RELATED APPLICATION

This application claims the priority benefit of Taiwan Patent Application Serial Number 100142660, filed on Nov. 22, 2011, the full disclosure of which is incorporated herein by reference.

BACKGROUND

1. Field of the Disclosure

This disclosure generally relates to a user interface system and, more particularly, to a user interface system and an optical finger mouse system capable of simultaneously detecting a physiological characteristic of a user, a finger displacement and a finger contact status.

2. Description of the Related Art

As the optical finger mouse has a relatively small size, it is suitable for being applied to portable electronic devices. An optical finger mouse can be used to detect an intensity variation of reflected light from a finger surface of a user so as to identify a finger contact status and a finger displacement with respect to a touch surface. However, with the development of industry, users spend more and more time on utilizing portable electronic devices that puts a lot of stress on their bodies. Therefore, if a portable electronic device also has the function of detecting physiological characteristics of a user and is able to give a warning when necessary, overuse of the portable electronic devices can then be avoided.

Conventional pulse oximeters utilize a noninvasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variation of the penetrating light of the two wavelengths is detected, the blood oxygenation can be calculated according to equation (1):

$$\text{Oxygen saturation} = 100\% \times [HbO_2]/([HbO_2]+[Hb]) \quad (1)$$

wherein $[HbO_2]$ is an oxyhemoglobin concentration; and $[Hb]$ is a deoxyhemoglobin concentration.

Figure 1:
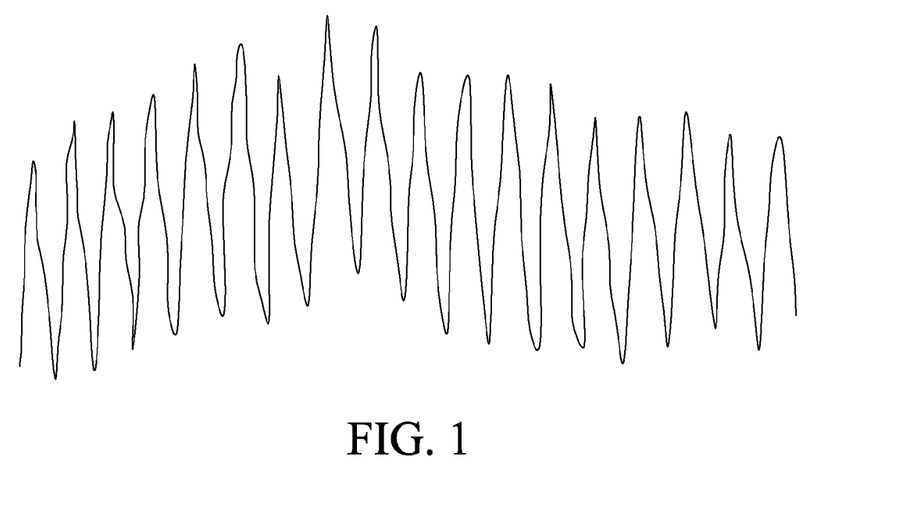
FIG. 1 shows a schematic diagram of an intensity variation of the penetrating light detected by pulse oximeters.

Generally, the intensity variation of the penetrating light of the two wavelengths detected by a pulse oximeter is similar to FIG. 1. This is because blood vessels will expand and contract with heartbeats such that the blood volume that the light beams pass through will change to accordingly change the ratio of light energy being absorbed. Therefore, the absorptivity of blood of different light spectra can be calculated according to the intensity information changing continuously so as to calculate the concentration information, e.g. the oxyhemoglobin and deoxyhemoglobin concentration, respectively. Finally, the blood oxygenation can be calculated according to equation (1).

However, as conventional pulse oximeters detect the intensity variation of the penetrating light, different intensity signals will be detected by detecting different parts of the human body. In addition, when the part of the human body being detected has a movement, a disturbed signal can be detected such that it is not possible to calculate correct physiological characteristics. Therefore, conventional pulse oximeters cannot be applied to portable electronic devices or devices operated in a moving state.

Accordingly, the present disclosure provides a user interface system and an optical finger mouse system that may simultaneously detect physiological characteristics of a user, a finger displacement and a finger contact status, and eliminate the signal noise caused by the movement.

SUMMARY

It is an object of the present disclosure to provide a user interface system and an optical finger mouse system that may simultaneously calculate a finger displacement, a finger contact status and a physiological characteristic of a user by analyzing reflected light signals from a finger.

It is another object of the present disclosure to provide a user interface system and an optical finger mouse system that may simultaneously detect a finger displacement, a finger contact status and a physiological characteristic of a user, and has a mechanism of eliminating interference from ambient light sources.

It is another object of the present disclosure to provide a user interface system and an optical finger mouse system that may simultaneously detect a finger displacement, a finger contact status and a physiological characteristic of a user, and has the mechanism of denoising and reducing transmission bandwidth.

It is another object of the present disclosure to provide a user interface system and an optical finger mouse system that may simultaneously detect a finger displacement, a finger contact status and a physiological characteristic of a user, and has the mechanism of regulating system frequency.

It is another object of the present disclosure to provide a user interface system and an optical finger mouse system that may simultaneously detect a finger displacement, a finger contact status and a physiological characteristic of a user, and enter a sleep mode after idling for a predetermined time period.

It is another object of the present disclosure to provide a user interface system and an optical finger mouse system that may simultaneously detect a finger displacement, a finger contact status and a physiological characteristic of a user, and the physiological characteristic may be abandoned or ignored when the finger displacement is too large.

It is another object of the present disclosure to provide a user interface system and an optical finger mouse system that may simultaneously detect a finger displacement, a finger contact status and a physiological characteristic of a user, and has a mechanism of checking data transmission between the master device and the slave device.

The present disclosure provides a user interface system including a slave device and a master device. The slave device is configured to provide light of two different wavelengths to illuminate a finger, receive reflected light from the finger to generate a plurality of first image frames and second image frames corresponding to on-states of the light of two different wavelengths, calculate and output a first image data associated with a predetermined number of the first image frames and a second image data associated with a predetermined number, of the second image frames. The master device is configured to calculate a displacement and a physiological characteristic according the first image data and the second image data.

The present disclosure further provides an optical finger mouse system including an optical detection device and a host. The optical detection device includes a first light source, a second light source, a light control unit, an image sensor and a processing unit. The first light source provides light of a first wavelength to a finger. The second light source provides light of a second wavelength to the finger. The light control unit is configured to control on-states and off-states of the first light source and the second light source. The image sensor is configured to receive reflected light from the finger at a sampling frequency to generate a plurality of first image frames corresponding to the on-states of the first light source and a plurality of second image frames corresponding to the on-states of the second light source. The processing unit is configured to calculate and output a first image data associated with a predetermined number of the first image frames and a second image data associated with a predetermined number of the second image frames. The host is configured to receive and check the first image data and the second image data to accordingly calculate a displacement and a physiological characteristic.

The present disclosure further provides a user interface system including an optical finger mouse and a host. The optical finger mouse is configured to provide light of two different wavelengths to illuminate a finger, receive reflected light from the finger to generate a plurality of first image frames and second image frames corresponding to on-states of the light of two different wavelengths, calculate and output a first image data associated with a predetermined number of the first image frames and a second image data associated with a predetermined number of the second image frames. The host includes a processing unit and a response unit. The processing unit is configured to calculate a displacement and a physiological characteristic according to the first image data and the second image data. The response unit is configured to respond the displacement and the physiological characteristic.

In the user interface system and optical finger mouse system of the present disclosure, the physiological characteristic includes a blood oxygenation and a heart rate. In the present disclosure, the movement informant and the physiology information are separated by means of independent component analysis (ICA) or blind source separation (BSS) so as to effectively eliminate the signal noise caused by the movement of the part of human body being detected.

In the user interface system of the present disclosure, the slave device may be a mouse, a remote controller, a keyboard, an optical distance measuring device or other electronic peripheral devices; and the master device may be a television, a projection device, a game machine system or a computer system.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

Figure 2A:
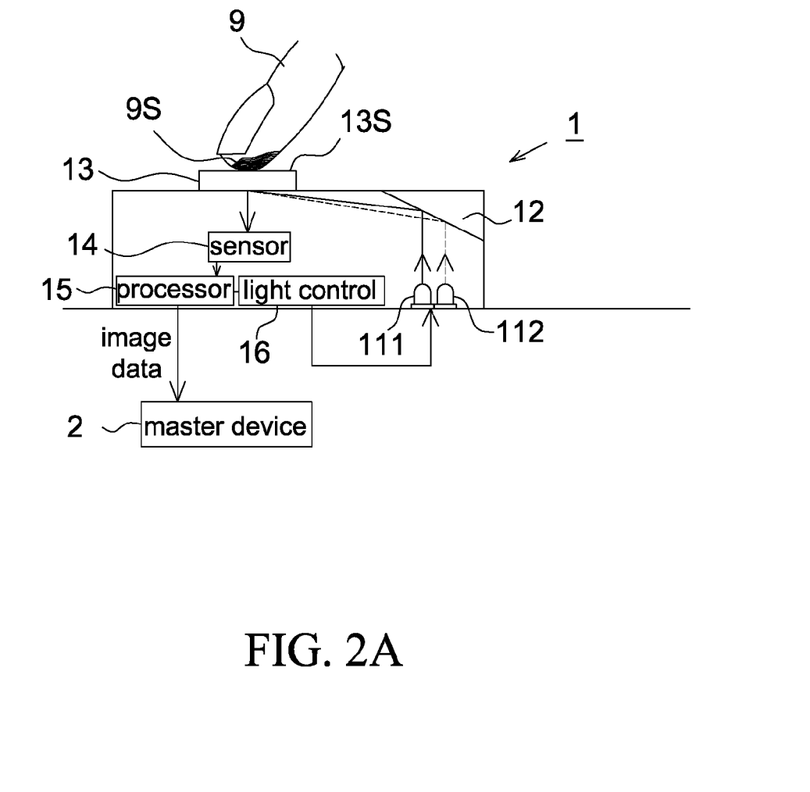
FIG. 2A shows a schematic diagram of the user interface system according to an embodiment of the present disclosure.

Please refer to FIG. 2A, it shows a schematic diagram of the user interface system according to an embodiment of the present disclosure which includes a slave device 1 and a master device 2. The slave device 1 is preferably an electronic peripheral device; and the master device 2 is preferably an electronic device having a response device for responding the output of the slave device 1 (e.g. performing cursor control, software execution and/or physiological state display), wherein the response device may be a display device, a lamp device, a seven-segment display and/or a sound device; and the electronic device may be a portable electronic device or a home appliance. In one embodiment, the user interface system may be an optical finger mouse system, wherein the slave device 1 may be an optical detection device and the master device 2 may be a host communicating with the slave device 1 wired or wirelessly. In another embodiment, the user interface system may include a finger mouse device and a host, wherein the host may further include a response unit configured to respond the information outputted from the finger mouse device.

The user interface system of the present disclosure is configured to detect a displacement and a contact status of a finger 9 of a user and a physiological characteristic of the user, such as a blood oxygenation and/or a heart rate. Generally, the user interface system starts to calculate the displacement and the physiological characteristic when identifying that the contact status is a touch state (i.e. the finger 9 being in contact with the user interface system).

The slave device 1 includes two light sources 111 and 112, a light guide 12, a touch member 13, an image sensor 14, a first processing unit 15 and a light control unit 16. In FIG. 2A, the spatial relationship between every component is only exemplary and not used to limit the present disclosure. The two light sources 111 and 112 may be light emitting diodes or laser diodes and respectively emit light of different wavelengths. Preferably, said different wavelengths are the two wavelengths used in conventional pulse oximeters, e.g. red light of wavelength about 660 nm and infrared light of wavelength about 905, 910 or 940 nm. It is appreciated that the wavelengths mentioned herein are the center wavelength of respective illumination spectrum of the two light sources.

The light guide 12 is configured to direct the light emitted by the light sources 111 and 112 to the touch member 13. The light guide 12 is not limited to a reflecting surface, and it may allow the light emitted by the light sources 111 and 112 to penetrate through and transmit to the touch member 13. In other embodiments, if the light emitted from the light sources 111 and 112 can directly impinge on the touch member 13, the light guide 12 may not be implemented.

The touch member 13 has a touch surface 13S for the finger 9 to operate thereon, and the touch member 13 is preferably transparent to the light emitted by the light sources 111 and 112 such that when the finger 9 approaches or touches the touch surface 13S, the light emitted by the light sources 111 and 112 is reflected. It is appreciated that an area of the touch surface 13S may be larger or smaller than that of the finger surface 9S.

The image sensor 14 receives, with a sampling parameter, reflected light from the touch member 13 (more specifically from the finger surface 9S) so as to generate a plurality of image frames, which may have a size of 16×16, wherein the sampling parameter may include an exposure time and an image gain, but not limited thereto. It is appreciated that in FIG. 2A the user interface system may further include a lens or lens set configured to guide the reflected light to the image sensor 14 so as to improve the sensing efficiency of the image sensor 14. The image sensor 14 is preferably an active matrix sensor, e.g. a CMOS image sensor, but it may also be other devices for detecting images.

The first processing unit 15 calculates and outputs an image data associated with a predetermined number of the image frames, e.g. a sum of M image frames, an average of M image frames, a normalized sum of M image frames or a normalized average of M image frames; i.e. every time the image sensor 14 outputs M image frames, the first processing unit 15 calculates and outputs a sum or an average of the M image frames, or further normalizes the sum or the average of the M image frames (described later). In other words, one image data refers processed (e.g. summation, average and/or normalization) image frames. The master device 2 calculates a displacement and a contact status of the finger 9 with respective to the touch surface 13S and a physiological characteristic of the user according to the image data.

The light control unit 16 is coupled to the first processing unit 15 and configured to control the ON/OFF (described later) of the light sources 111 and 112 in cooperation with the image capturing of the image sensor 14.

Figure 2B:
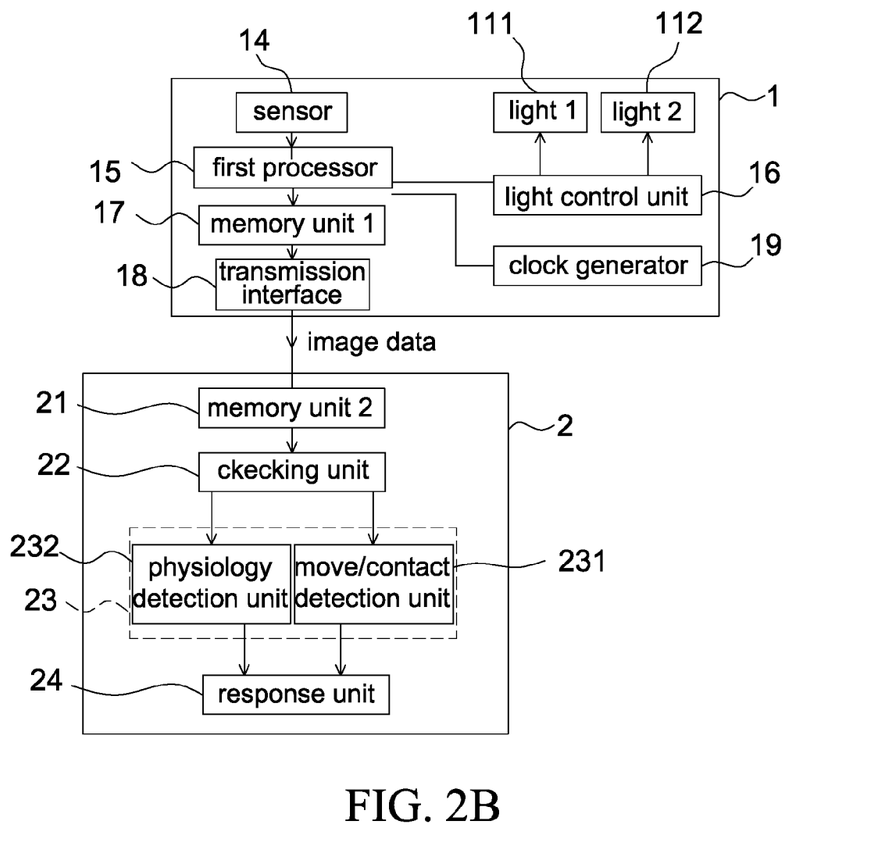
FIG. 2B shows a schematic block diagram of the user interface system according to an embodiment of the present disclosure.

Please refer to FIGS. 2A and 2B, FIG. 2B shows a schematic block diagram of the user interface system according to the embodiment of the present disclosure. The user interface system includes the slave device 1 and the master device 2. The slave device 1 includes a first light source 111, a second light source 112, the image sensor 14, the first processing unit 15, the light control unit 16, a first memory unit 17, a transmission interface 18, and a clock generator 19. The master device 2 includes a second memory unit 21, a checking unit 22, a second processing unit 23 and a response unit 24, wherein because the second processing unit 23 has multifunction, it may further include a move/contact detection unit 231 configured to detect the displacement and contact status of the finger 9 with respect to the touch surface 13S and a physiology detection unit 232 configured to detect the physiological characteristic of the user. That is, the second processing unit 23 may be a single element or composed of two elements.

The first light source 111 may emit red light of wavelength about 660 nm and the second light source 112 may emit infrared light of wavelength about 905, 910 or 940 nm. Broadly speaking, the first light source 111 and the second light source 112 respectively emit light of the two wavelengths used in conventional pulse oximeters. The light control unit 16 controls the ON/OFF (i.e. on states and off states) of the first light source 111 and the second light source 112 such that the image sensor 14 may receive reflected light from the finger 9 at a sampling frequency to generate a plurality of first image frames corresponding to on-states of the first light source 111 and a plurality of second image frames corresponding to on-states of the second light source 112. The first processing unit 15 calculates a first image data associated with a predetermined number of the first image frames, e.g. a first image sum, a first image average, a normalized first image sum or a normalized first image average of M first image frames, and calculates a second image data associated with a predetermined number of the second image frames, e.g. a second image sum, a second image average, a normalized second image sum or a normalized second image average of M second image frames. The first memory unit 17 may be a memory buffer and configured to store the first image data and the second image data obtained by the first processing unit 15. The transmission interface 18 is configured to wired or wirelessly transmit the first image data and the second image data stored in the first memory unit 17 to the master device 2, wherein wired and wireless communication are well known and thus details thereof will not be described herein. It should be mentioned that if the data communication between the slave device 1 and the master device 2 is accurate enough, the first memory unit 17 may not be implemented. The clock generator 19 is configured to provide the system clock of the slave device 1.

The second memory unit 21 is configured to store the first image data and the second image data received from the slave device 1. The checking unit 22 is configured to check oversampled data or data loss of the first image data and the second image data. If the first image data and the second image data have oversampled data, the oversampled data is directly abandoned. If the first image data and the second image data have data loss, the lost data may be recovered by interpolation. If the first image data and the second image data do not have these problems, they are directly transmitted to the second processing unit 23. It is appreciated that since the checking unit 23 has multifunction, the checking, abandon and interpolation functions may be executed by a single component or respectively executed by a plurality of components. The second processing unit 23 (or the move/contact detection unit 231) is configured to calculate the displacement and the contact status of the finger 9 with respective to the touch surface 13S according to the first image data and the second image data. The second processing unit 23 (or the physiology detection unit 232) is configured to calculate the physiological characteristic of the user according to the first image data and the second image data. The response unit 24 is configured to display and/or respond the displacement, contact status and physiological characteristic obtained by the second processing unit 23.

In one embodiment, the master device 2 may be a television, a projection device, a computer system, a game machine system or other electronic devices having a response unit. The slave device 1 may be a remote controller, a mouse, a keyboard, an optical distance measuring device or other electronic peripheral devices. In other words, the slave device 1 and the master device 2 are wired or wirelessly coupled to each other so as to form a signal device (e.g. a portable device) or a plurality of devices (e.g. a home appliance system). The slave device 1 sends the first image data corresponding to the on-states of the first light source 111 and the second image data corresponding to the on-states of the second light source 112. The master device 2 calculates and/or responds the displacement, contact status and physiological characteristic according to the first image data and the second image data.

Therefore, the slave device 1 of the present disclosure may be incorporated with a master device 2 having a response device 24 such that the master device 2 may show the physiological characteristic for reference when a user uses the slave device 1 to control a cursor shown on the response unit 24 or a application executed by the master device 2, and may give a warning when the physiological characteristic indicates that the user is in a fatigue state (e.g. according to a value of the physiological characteristic), wherein the method of showing the physiological characteristic and the warning may be implemented by, for example, showing on a screen, representing by a lamp device or by sound controlled by a software.

In other embodiments, the slave device 1 may include two image sensors configured to detect the light of two different wavelengths respectively, and an optical bandpass filter may be integrated on one or two of the image sensors in order to select the desired spectrum.

Sampling Mechanism

The user interface system of the present disclosure includes two light sources and may perform two functions simultaneously, wherein the function of detecting the displacement and contact status may use the image frames associated with any wavelength without limitation, but the function of detecting the physiological characteristic needs to be performed using the image frames associated with specific wavelength. First, the sampling mechanism of the image frames in the present disclosure is illustrated hereinafter.

Figure 3:
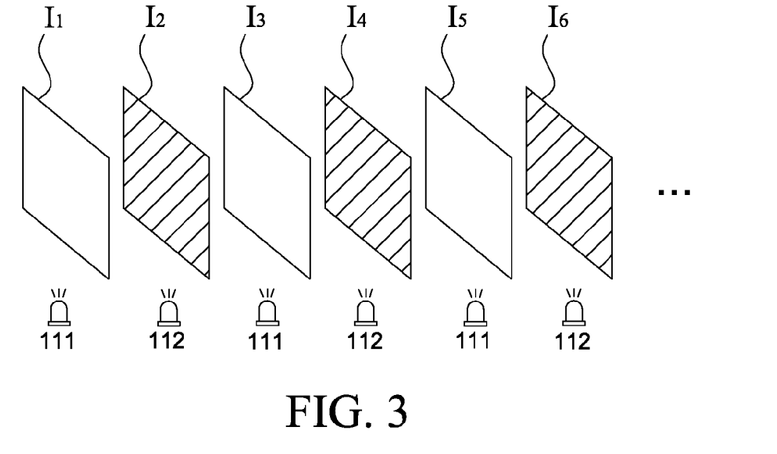
FIG. 3 shows a schematic diagram of the image frames captured by the image sensor of the user interface system according to the embodiment of the present disclosure.

In one embodiment, the light control unit 16 controls the first light source 111 and the second light source 112 to turn on alternatively. The image sensor 14 captures image frames at a high and fixed sampling frequency (e.g. 3,000 frames/sec) and synchronizing to the turning on (i.e. the on-states) of the first light source 111 or the second light source 112, and outputs a plurality of image frames $I_1$ to $I_6$ . . . as shown in FIG. 3 to the first processing unit 15, wherein the image frames $I_1$ to $I_6$ . . . include first image frames $I_1$, $I_3$, $I_5$ . . . corresponding to the on-states of the first light source 111 and second image frames $I_2$, $I_4$, $I_6$ . . . corresponding to the on-states of the second light source 112. The first processing unit 15 calculates a first image data of M first image frames $I_1$, $I_3$, $I_5$ . . . , e.g. a first image sum $(I_1+I_3+I_5+ \ldots )$, a first image average $(I_1+I_3+I_5+ \ldots )/M$, a normalized first image sum $(I_1+I_3+I_5+ \ldots )/(\text{sampling parameter})$ or a normalized first image average $(I_1+I_3+I_5+ \ldots )/(M \times \text{sampling parameter})$, and calculates a second image data of M second image frames $I_2$, $I_4$, $I_6$, . . . , e.g. a second image sum $(I_2+I_4+I_6+ \ldots )$, a second image average $(I_2+I_4+I_6+ \ldots )/M$, a normalized second image sum $(I_2+I_4+I_6+ \ldots )/(\text{sampling parameter})$ or a normalized second image average $(I_2+I_4+I_6+ \ldots )/(M \times \text{sampling parameter})$. In one embodiment, the first processing unit 15 processes ten of the first and second image frames at a time, i.e. M=10, but not limited thereto.

The second processing unit 23 (or the move/contact detection unit 231) may identify a contact status and calculate a displacement according to the first and second image data stored in the second memory unit 21, e.g. identifying whether the finger 9 approaches or touches the touch surface 13S according to a comparison result of comparing a brightness value of the first and second image data with at least one brightness threshold, wherein when the brightness value of the image data is larger or smaller than the brightness threshold, a touch state is entered. After entering the touch state, the second processing unit 23 may calculate the displacement according to the correlation between two first image data, between one first image data and one second image data, or between two second image data. It should be mentioned that although the method of identifying the contact status and calculating the displacement may use conventional methods, the identification process and the calculation process in the present disclosure need to use the image data corresponding to the reflected light of two different wavelengths and thus are different from conventional navigation devices.

The second processing unit 23 (or the physiology detection unit 232) may calculate an intensity variation of first image data according to the first image data, and calculates an intensity variation of second image data according to the second image data (described later), and accordingly calculate the absorptivity of blood in two spectra so as to obtain $[HbO_2]$ and $[Hb]$. Finally, the blood oxygenation may be calculated according to equation (1), and the heart rate may also be calculated according to a comparison result of comparing the intensity variation of first image data and/or the intensity variation of second image data with at least one pulse threshold.

Figure 4:
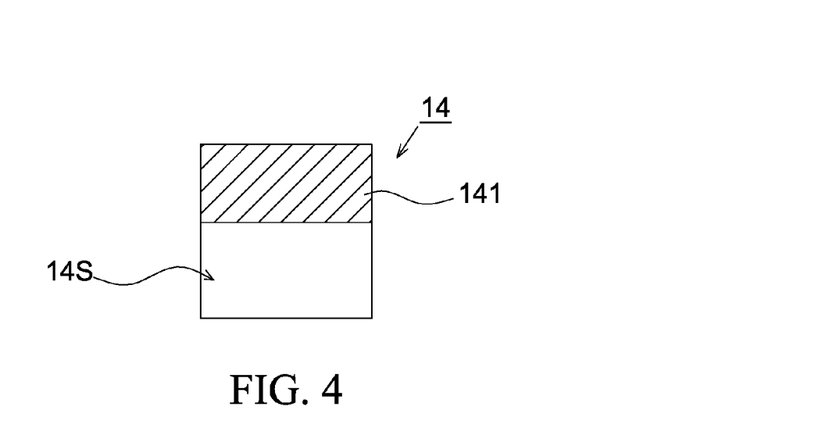
FIG. 4 shows a schematic diagram of the image sensor of the user interface system according to the embodiment of the present disclosure, wherein an optical filter is disposed in front of a part of a sensing surface thereof.

In another embodiment, the light control unit 16 controls the first light source 111 and the second light source 112 to turn on simultaneously and synchronizing to the image capturing of the image sensor 14; that is, the image sensor 14 may receive reflected light of two wavelengths simultaneously. Therefore, in this embodiment an optical filter 141 is further disposed in front of at least a part of a sensing surface 14S of the image sensor 14 as shown in FIG. 4, wherein the optical filter 141 may be an optical bandpass filter to allow the part of the sensing surface 14S behind the optical filter 141 to only receive the spectrum of light of the first light source 111 or the second light source 112 such that the second processing unit 23 (or the move/contact detection unit 231 and the physiology detection unit 232) may distinguish the first image data (i.e. the part of the image frame associated with the first light source 111) and the second image data (i.e. the part of the image frame associated with the second light source 112). It is appreciated that in the present disclosure the position and the area of the optical filter 141 are not limited to those shown in FIG. 4.

In this manner, the second processing unit 23 (or the move/contact detection unit 231) may also calculate a contact status and a displacement according to the first image data and the second image data. The second processing unit 23 (or the physiology detection unit 232) may also calculate an intensity variation of first image data according to the first image data, an intensity variation of second image data according to the second image data, and the blood oxygenation and the heart rate according to the two intensity variations.

It is appreciated that as the sensing efficiency of the image sensor 14 toward light of different wavelengths may be different or illumination brightness values of the first light source 111 and the second light source 112 may not be exactly identical, the brightness value of the image frames captured by the image sensor 14 may be previously adjusted (e.g. by adjusting the sampling parameter, such as an exposure time and an image gain, of the image frames corresponding to different wavelengths) before shipment such that the image frames initially outputted by the image sensor 14 may have substantially identical brightness values so as to improve the identification accuracy.

In this embodiment, the slave device 1 provides light of two different wavelengths to illuminate a finger surface 9S, captures reflected light from the finger surface 9S to generate a plurality of image frames, calculates and outputs an image data associated with a plurality number of the image frames. The master device 2 calculates the contact status, displacement and physiological characteristic according to the image data.

Mechanism of Eliminating Ambient Light Interference

In FIG. 2A, as the touch member 13 and the finger 9 are light transmissive, the ambient light outside the slave device 1 can penetrate the finger 9 and the touch member 13 and then be received by the image sensor 14 to degrade the image quality of the image frames captured thereby. In the present disclosure, the light control unit 16 may control the first light source 111 and the second light source 112 to turn off (i.e. the off-states) in predetermined time intervals.

Figure 5:
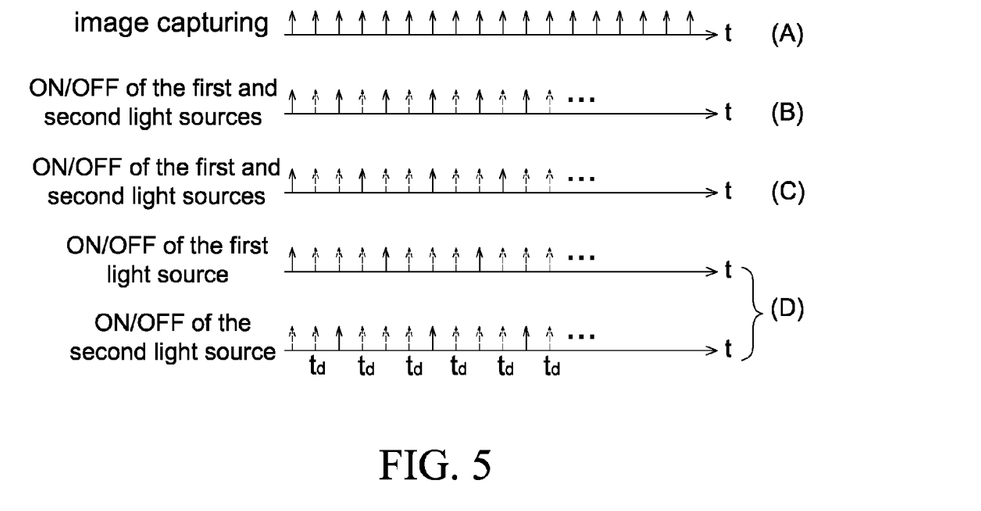
FIG. 5 shows a schematic diagram of the image capturing of the image sensor and the ON/OFF of the light sources in the user interface system according to the embodiment of the present disclosure.

For example please refer to FIG. 5, it shows a schematic diagram of the image capturing of the image sensor 14 and the ON/OFF of the first light source 111 and the second light source 112, wherein in FIGS. 5(B)-5(D) solid arrows denote the on-states of the light sources and dashed arrows denote the off-states of the light sources. FIG. 5(A) shows that the image sensor 14 captures image frames at a fixed sampling frequency. FIG. 5(B) shows that the first light source 111 and the second light source 112 are alternatively turned on and turned off at the same time, and thus the image sensor 14 may alternatively capture bright image frames (i.e. corresponding to the on-states of the light sources) and dark image frames (i.e. corresponding to the off-states of the light sources). FIG. 5(C) shows that the first light source 111 and the second light source 112 are simultaneously turned on once after turning off two image periods, and this embodiment is generally for a lower displacement of the finger 9. As mentioned above, when the first light source 111 and the second light source 112 are turned on simultaneously (FIGS. 5(B) and 5(C)), the image sensor 14 further includes an optical filter 141 (as shown in FIG. 4) for spatially distinguishing the image frame associated with different light sources such that one part of the image sensor 14 may sense reflected light associated with the first light source 111 and the other part thereof may sense reflected light associated with the second light source 112.

When the finger 9 touches or approaches the touch surface 13S, the bright image frames, which are associated with the on-states of the light sources, include components of (reflected light from finger+stray light+ambient light), and the dark image frames, which are associated with the off-states of the light sources, include only the component of (ambient light). Therefore, if a dark image frame is subtracted from a bright image frame, the interference from the ambient light can be effectively eliminated. The first processing unit 15 may calculate a differential image data according to differential images between the bright image frames and the dark image frames, e.g. a differential image sum, a differential image average, a normalized differential image sum and a normalized differential image average of M differential images. The second processing unit 23 then calculates the displacement, contact status and physiological characteristic according to the differential image data.

Please refer to FIG. 5(D), it shows an embodiment in which the first light source 111 and the second light source 112 are turned on alternatively. In this embodiment, in order to allow the image sensor 14 to be able to capture dark image frames, the light control unit 16 controls the first light source 111 and the second light source 112 to alternatively turn on every other image frame, e.g. the two light sources are both turned off at time $t_d$ in FIG. 5(D). Accordingly, the first processing unit 15 may calculate a differential first image (i.e. bright first image frame−dark image frame) and a differential second image (i.e. bright second image frame−dark image frame), and calculate a differential first image data and a differential second image data. The second processing unit 23 may calculate the displacement, contact status and physiological characteristic according to the differential image data. As mentioned above, if the first light source 111 and the second light source 112 are turned on alternatively, the image sensor 14 may temporally distinguish the image frames associated with different light sources.

In this embodiment, the light control unit 16 controls the first light source 111 and the second light source 112 to turn on simultaneously or alternatively and the image sensor 14 is able to capture dark image frames when both the light sources are turned off. The interference from ambient light is eliminated by calculating a difference between bright and dark image frames. It is appreciated that the on-states and off-states of each light source shown in FIG. 5 are only exemplary and not used to limit the present disclosure.

Mechanism of Denoising and Reducing Transmission Bandwidth

As the image frames captured by the image sensor 14 generally include noise which is randomly distributed in the image frames being captured. Therefore, in the present disclosure the first processing unit 15 calculates a sum of M image frames to increase the signal-to-noise ratio (SNR) thereby improving the calculation accuracy of the physiological characteristic. For example, it is able to calculate a sum of 10 image frames and every group of 10 image frames may have partially repeated image frames or totally different 10 image frames. Therefore, a sum of image frames may be obtained every ten image frames, and in addition to the SRN is improved, the transmission bandwidth between the slave device 1 and the master device 2 is also reduced since the image sensor 14 preferably has a high sampling frequency. In other embodiments, the sum of image frames may be averaged by a number of the image frames being added. It is appreciated that if the first light source 111 and the second light source 112 are turned on alternatively, the sum of image frames in this embodiment may be a sum of first image frames (e.g. $I_1+I_3+I_5+\ldots$ as shown in FIG. 3) and a sum of second image frames (e.g. $I_2+I_4+I_6+\ldots$ as shown in FIG. 3) since two intensity variations need to be calculated respectively. However, if the first light source 111 and the second light source 112 are turned on simultaneously, the sum of image frames in this embodiment is a sum of successive image frames (e.g. $I_1+I_2+I_3+I_4+I_5+I_6+\ldots$ as shown in FIG. 3), and the two intensity variations may be distinguished by post-processing to accomplish spatially distinguishing. In addition, if the mechanism of eliminating ambient light interference described above is incorporated in this embodiment, the sum of first image frames is a sum of differential first images, the average of first image frames is an average of differential first images, the sum of second image frames is a sum of differential second images, the average of second image frames is an average of differential second images; that is, the process of eliminating ambient light interference is performed first and then the process of denoising is performed successively. In other embodiments, it is able to only perform the mechanism of denoising.

As mentioned above, the image sensor 14 may capture image frames with different sampling parameters, e.g. the image sensor 14 may have different absorptions of light at different wavelengths, and thus different sampling parameters, such as different exposure times and different image gains, may be used to make the first image frame and the second image frame have substantially identical initial brightness values in order to correctly perform the post-processing on the image frames; that is, the sampling parameters associated with capturing the first image frames and the second image frames may be different. In the present disclosure, in order to eliminate the influence of different sampling parameters, a sum of M image frames or an average of M image frames may be normalized by the sampling parameter, e.g. (a sum of M image frames/sampling parameter) or (an average of M image frames/sampling parameter), wherein M is a positive integer. If the mechanism of eliminating ambient light interference described above is incorporated in this embodiment, the normalized sum of first image frames is a normalized sum of differential first images, the normalized average of first image frames is a normalized average of differential first images, the normalized sum of second image frames is a normalized sum of differential second images, the normalized average of second image frames is a normalized average of differential second images.

Mechanism of Checking Data

In the present disclosure, as the calculation of physiology information needs accurate image data, the checking unit 22 of the master device 2 checks the image data transmitted from the slave device 1. When the image data has oversampled data, the oversampled data is abandoned. When the image data has data loss, the lost data is recovered by interpolation so as to avoid detection error.

Calculating Physiological Characteristics

Corresponding to the on-states of different light sources, the image frames captured by the image sensor 14 may contain physiology information and movement information at the same time. Therefore, in the present disclosure the second processing unit 23 (or the physiology detection unit 232) has to separate two types of information at first and then is able to calculate the physiological characteristic correctly. In the present disclosure, the second processing unit 23 may separate the two types of information according to, for example, independent component analysis (ICA) or blind source separation (BSS).

Figure 6:
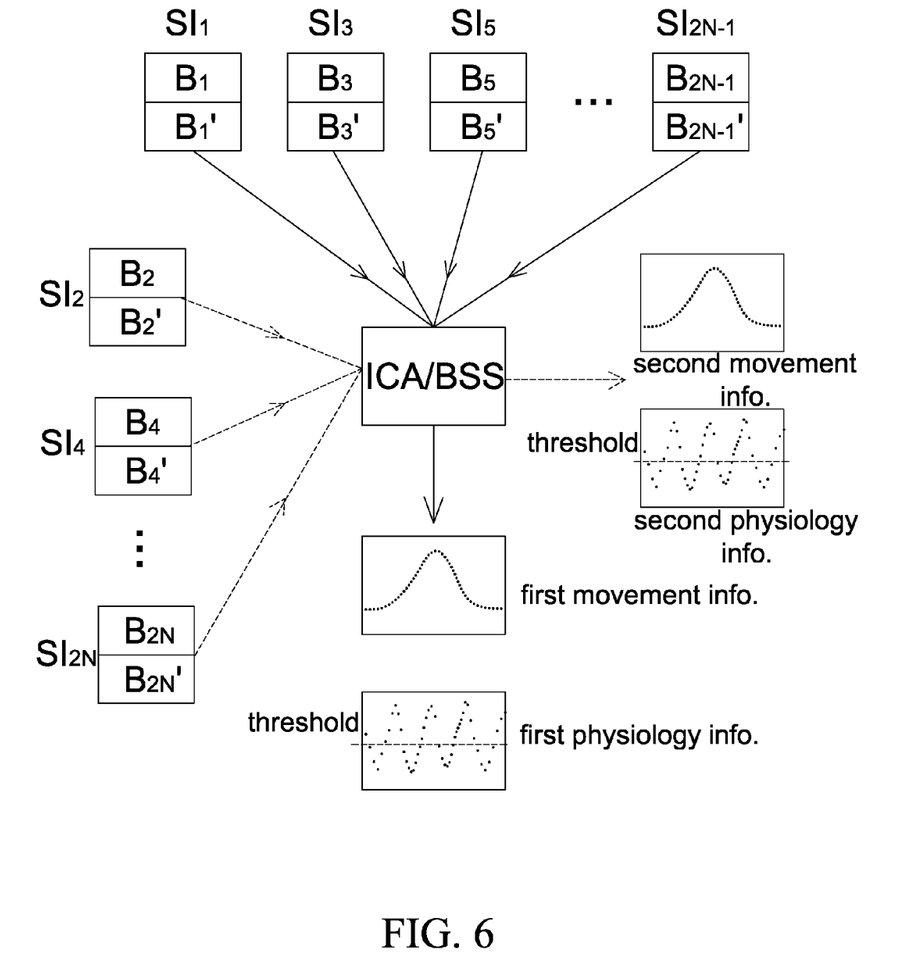
FIG. 6 shows a schematic diagram of separating the movement information and the physiology information by the second processing unit of the user interface system according to the embodiment of the present disclosure.

Please refer to FIGS. 3 and 6, first taking the first image frames $I_1$, $I_3$, $I_5$ . . . shown in FIG. 3 as an example, each of the first image data associated with the first image frames (e.g. a sum of M original first image frames or a sum of M first image frames processed by the mechanism of eliminating ambient light interference and/or normalization) is divided into at least two parts and an average brightness of each part is calculated, e.g. the image data $SI_1$ is divided into two parts respectively having an average brightness $B_1$ and $B_1'$; the image data $SI_3$ is divided into two parts respectively having an average brightness $B_3$ and $B_3'$; . . . ; the image data $SI_{2N-1}$ is divided into two parts respectively having an average brightness $B_{2N-1}$ and $B_{2N-1}'$, but the image data may be divided into more than two parts in other embodiments, wherein the image data $SI_1$ may be $(I_1+I_3+ \ldots +I_{19})$, $(I_1+I_3+ \ldots +I_{19})/10$, $(I_1+I_3+ \ldots +I_{19})/$(sampling parameter), $(I_1+I_3+ \ldots +I_{19})/(10 \times$sampling parameter); the image data $SI_3$ may be $(I_{21}+I_{23}+ \ldots +I_{39})$, $(I_{21}+I_{23}+ \ldots +I_{39})/10$, $(I_{21}+I_{23}+ \ldots +I_{39})/$(sampling parameter), $(I_{21}+I_{23}+ \ldots +I_{39})/(10 \times$sampling parameter); . . . . Next, a first movement informant and a first physiology information is separated from the divided image data according to the independent component analysis (ICA) or blind source separation (BSS) method as shown in FIG. 6, and each of the information is shown as a curve of intensity variation. In the present disclosure the movement information is abandoned and the physiological characteristic is calculated only according to the physiology information. It is appreciated that as the sampling frequency of the image sensor 14 is much higher than the heart rate, the separated physiology information is shown as a curve of the intensity variation changed with the pulse beating (i.e. similar to FIG. 1), and the separated movement information is not limited to that shown in FIG. 6. In addition, the two parts divided from the image data are not necessary to be the upper and lower parts of the image data. In addition, as it is necessary to respectively calculate the physiology information associated with two wavelengths, the aforementioned separation process is performed respectively on the first image data $SI_1$, $SI_3$, $SI_5$ . . . (i.e. corresponding to the on-states of the first light source) and the second image data $SI_2$, $SI_4$, $SI_6$ . . . (i.e. corresponding to the on-states of the second light source).

It should be mentioned that the displacement and the contact status of the finger 9 are calculated by the second processing unit 23 (or the move/contact detection unit 231) directly according to the original first image data and second image data without using the separated movement information. The ICA and BSS methods are mainly configured to separate combined signals so as to eliminate the signal noise caused by the movement.

In the present disclosure, the second processing unit 23 (or the move/contact detection unit 231) further calculates a heart rate according to a comparison result of comparing at least one pulse threshold with a first intensity variation (i.e. the first physiology information) and/or a second intensity variation (i.e. the second physiology information).

Mechanism of Regulating System Frequency

In order to reduce the system cost, the clock generator 19 may use a RC oscillator circuit. Although the RC oscillator circuit has a lower cost, it also has a lower precision as its oscillating frequency can change with the manufacturing process and operating temperature. The crystal oscillator may also be utilized in other embodiments. In calculating physiological characteristics, a precise system frequency is necessary (e.g. in calculating the heart rate). Therefore, preferably a reference to regulate the oscillating frequency of the clock generator 19 of the slave device 1 may be constructed before shipment; for example, an external light source having a precise lighting frequency may be attached to the touch surface 13S of the touch member 13 to allow the image sensor 14 to detect the intensity variation of the external light source; then, a difference between the oscillating frequency of the clock generator 19 under different operating temperatures and the precise lighting frequency may be recorded previously to be served as a system frequency calibration parameter and pre-stored in the first memory unit 17. And the system frequency can be precisely adjusted based on the system frequency calibration parameter when necessary.

Sleep Mode

The user interface system of the present disclosure may enter a sleep mode after idling for a predetermined time period. For example, when the second processing unit 23 identifies that a finger 9 does not approach or touch the touch surface 13S within the predetermined time period, the sleep mode is entered.

Mechanism of Removing Physiological Characteristic

Although the second processing unit 23 of the user interface system of the present disclosure may calculate the displacement and the physiological characteristic simultaneously, accurate physiological characteristics can only be obtained when the displacement is relatively small. Therefore, in the present disclosure the second processing unit 23 may previously identify whether the displacement is larger than a predetermined value (i.e. a displacement threshold). When the displacement is larger than the predetermined value, the image frames captured by the image sensor 14 are only used to calculate the displacement or to identify the contact status but not used to calculate the physiological characteristic; or even though the physiological characteristic is calculated, the physiological characteristic is not responded by the response unit 24.

Figure 7:
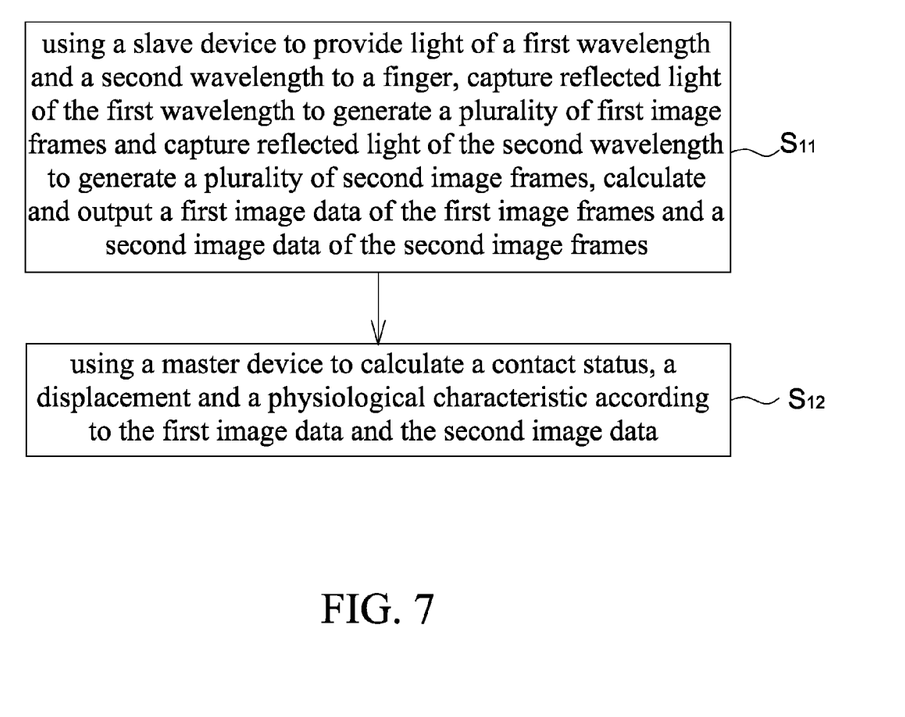
FIG. 7 shows a flow chart of the physiology detection method according to an embodiment of the present disclosure.

The present disclosure provides a method of detecting physiological characteristics according to reflected light from a finger surface including the steps of: using a slave device to provide light of a first wavelength and a second wavelength to a finger, capture reflected light of the first wavelength to generate a plurality of first image frames and capture reflected light of the second wavelength to generate a plurality of second image frames, calculate and output a first image data of the first image frames and a second image data of the second image frames (Step $S_{11}$); and using a master device to calculate a contact status, a displacement and a physiological characteristic according to the first image data and the second image data (Step $S_{12}$). In the physiology detection method of this embodiment, the definition of the first image data and second image data is defined above. In addition, details of every step are described above and thus details thereof will not be described herein.

The physiology detection method of the present disclosure may calculate a physiological characteristic through detecting the skin surface of a part of the human body. Therefore, the detection function may be executed only by replacing the finger 9 used in aforementioned embodiments by another part of the human body. The user interface system of the present disclosure has the mechanisms of denoising, reducing transmission bandwidth, checking data mistakes, eliminating ambient light interference, entering sleep mode and regulating system frequency. Said another part of the human body may be the part of the human body to be detected in conventional pulse oximeters.

As mentioned above, the conventional optical finger mouse can not detect the physiological characteristic of a user and the method of calculating the blood oxygenation for pulse oximeters cannot be applied to an optical finger mouse as it can not detect a moving object. Therefore, the present disclosure further provides a user interface system (FIGS. 2A and 2B) that can detect the finger displacement and the physiological characteristic of a user simultaneously, and can effectively eliminate the signal noise caused by movement and the interference from ambient light source, and further has the mechanisms of regulating the system frequency, checking data mistakes, reducing transmission bandwidth, entering sleep mode and removing invalid physiology information.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A user interface system configured to detect a displacement of a finger of a user and a physiological characteristic of the user, the user interface system comprising:
   a slave device configured to
      provide light of two different wavelengths to illuminate the finger,
      receive reflected light from the finger to generate a plurality of first image frames and second image frames corresponding to on-states of the light of two different wavelengths,
      calculate and output first image data associated with a first predetermined number of the first image frames and second image data associated with a second predetermined number of the second image frames; and
   a master device configured to
      calculate the displacement of the finger according to the correlation between the first image data and the second image data;
      divide each of the first image data into a first image area of the first image data and a second image area of the first image data, respectively calculate an average brightness of each of the first image area and the second image area such that one average brightness is obtained for each of the first and second image areas of the first image data, wherein the second image area is other than the first image area among the first image data;
      analyze, using an independent component analysis method, the average brightness of each of the first image area and the second image area of the first image data to obtain (i) a first movement information, which contains a first intensity variation of signal noise caused by movement, and (ii) a first physiology information;
      abandon all the first movement information to eliminate the signal noise caused by movement, without calculating the physiological characteristic according to the first movement information;
      divide each of the second image data into a third image area of the second image data and a fourth image area of the second image data, respectively calculate an average brightness of each of the third image area and the fourth image area such that one average brightness is obtained for each of the third and fourth image areas of the second image data, wherein the fourth image area is other than the third image area among the second image data;
      analyze, using the independent component analysis method, the average brightness of each of the third image area and the fourth image area of the second image data to obtain (a) a second movement information, which contains a second intensity variation of the signal noise caused by movement, and (b) a second physiology information;
      abandon all the second movement information to eliminate the signal noise caused by movement, without calculating the physiological characteristic according to the second movement information;
      calculate the physiological characteristic according to the first physiology information and the second physiology information when the calculated displacement of the finger does not exceed a displacement threshold; and
      not calculate the physiological characteristic according to the first image data and the second image data when the calculated displacement of the finger exceeds the displacement threshold.

2. The user interface system as claimed in claim 1, wherein
   the slave device is a mouse, a remote controller, a keyboard or an optical distance measuring device; and the master device is a television, a projection device, a game machine system or a computer system.

3. The user interface system as claimed in claim 1, wherein the physiological characteristic comprises a blood oxygenation and a heart rate.

4. The user interface system as claimed in claim 1, wherein the slave device further comprises:
a first light source configured to provide light of a first wavelength to the finger;
a second light source configured to provide light of a second wavelength to the finger, the second wavelength different from the first wavelength;
a light control unit configured to control on-states and off-states of the first light source and the second light source;
an image sensor configured to receive the reflected light from the finger at a sampling frequency to generate the first image frames and the second image frames; and
a first processing unit configured to calculate the first image data of the first predetermined number of the first image frames and the second image data of the second predetermined number of the second image frames.

5. The user interface system as claimed in claim 4, wherein
the first image data is a first image sum, a first image average, a normalized first image sum or a normalized first image average of the first predetermined number of the first image frames; and
the second image data is a second image sum, a second image average, a normalized second image sum or a normalized second image average of the second predetermined number of the second image frames.

6. The user interface system as claimed in claim 4, wherein
the light control unit is configured to enable the off-states of the first light source and the second light source for predetermined time intervals such that the image sensor captures a plurality of bright first image frames, a plurality of bright second image frames and a plurality of dark image frames; and
the first processing unit is configured to calculate the first image data and the second image data according to a difference between the bright first image frames and the dark image frames and according to a difference between the bright second image frames and the dark image frames.

7. The user interface system as claimed in claim 4, wherein
the light control unit is configured to alternatively enable the on-states of the first light source and the second light source such that the image sensor receives the reflected light associated with the first light source and the second light source alternatively; or
the light control unit is configured to simultaneously enable the on-states of the first light source and the second light source such that the image sensor receives the reflected light associated with the first light source and the second light source simultaneously, and the image sensor comprises an optical filter covering at least a part of a sensing surface thereof.

8. The user interface system as claimed in claim 1, wherein the master device further comprises:
a memory unit configured to store the first image data and the second image data received from the slave device;
a checking unit configured to check oversampled data and data loss of the first image data and the second image data; and
a second processing unit configured to calculate the displacement and the physiological characteristic.

9. The user interface system as claimed in claim 8, wherein the second processing unit is further configured to calculate a heart rate according to a comparison result of comparing at least one pulse threshold with at least one of the first physiology information and the second physiology information.

10. The user interface system as claimed in claim 1, wherein
the master device further comprises a response unit configured to respond to the displacement and the physiological characteristic; and
the response unit is at least one of a display device, a lamp device, a seven-segment display and a sound device.

11. The user interface system as claimed in claim 1, wherein the user interface system is configured to enter a sleep mode after idling for a predetermined time period.

12. The user interface system as claimed in claim 1, wherein the slave device further comprises a memory unit configured to store a system frequency calibration parameter.

13. The user interface system as claimed in claim 1, wherein the master device is further configured to compare a brightness value of the first image data and the second image data with at least one brightness threshold to identify a contact status.

14. The user interface system as claimed in claim 1, wherein the master device is configured to calculate the displacement according to two of the first image data, according to one of the first image data and one of the second image data, and according to two of the second image data.

15. An optical finger mouse system, comprising:
an optical detection device, comprising:
a first light source configured to provide light of a first wavelength to a finger of a user;
a second light source configured to provide light of a second wavelength to the finger, the second wavelength different from the first wavelength;
a light control unit configured to control on-states and off-states of the first light source and the second light source;
an image sensor configured to receive reflected light from the finger at a sampling frequency to generate a plurality of first image frames corresponding to the on-states of the first light source and a plurality of second image frames corresponding to the on-states of the second light source; and
a processing unit configured to calculate and output first image data associated with a first predetermined number of the first image frames and second image data associated with a second predetermined number of the second image frames; and
a host configured to
receive and check the first image data and the second image data;
calculate a displacement of the finger according to the correlation between the first image data and the second image data;
divide each of the first image data into a first image area of the first image data and a second image area of the first image data, respectively calculate an average brightness of each of the first image area and the second image area such that one average brightness is obtained for each of the first and second image areas of the first image data, wherein the second image area is other than the first image area among the first image data;

analyze, using an independent component analysis method, the average brightness of each of the first image area and the second image area of the first image data to obtain a first movement information, which contains a first intensity variation of signal noise caused by movement, and a first physiology information;

abandon all the first movement information to eliminate the signal noise caused by movement, without calculating the physiological characteristic according to the first movement information;

divide each of the second image data into a third image area of the second image data and a fourth image area of the second image data, respectively calculate an average brightness of each of the third image area and the fourth image area such that one average brightness is obtained for each of the third and fourth image areas of the second image data, wherein the fourth image area is other than the third image area among the second image data;

analyze, using the independent component analysis method, the average brightness of each of the third image area and the fourth image area of the second image data to obtain a second movement information, which contains a second intensity variation of the signal noise caused by movement, and a second physiology information;

abandon all the second movement information to eliminate the signal noise caused by movement, without calculating the physiological characteristic according to the second movement information;

calculate a physiological characteristic of the user according to the first physiology information and the second physiology information when the calculated displacement of the finger does not exceed a displacement threshold; and not calculate the physiological characteristic according to the first image data and the second image data when the calculated displacement of the finger exceeds the displacement threshold.

16. The optical finger mouse system as claimed in claim 15, wherein when the host detects that the first and second image data have oversampled data, the host is configured to discard the oversampled data; and when the host detects that the first and second image data have data loss, the host is configured to perform interpolation.

17. A user interface system, comprising:
an optical finger mouse configured to
provide light of two different wavelengths to illuminate a finger of a user,
receive reflected light from the finger to generate a plurality of first image frames and second image frames corresponding to on-states of the light of two different wavelengths,
calculate and output first image data associated with a first predetermined number of the first image frames and second image data associated with a second predetermined number of the second image frames; and a host, comprising:
a processing unit configured to
calculate a displacement of the finger according to the correlation between the first image data and the second image data, and
divide each of the first image data into a first image area of the first image data and a second image area of the first image data, respectively calculate an average brightness of each of the first image area and the second image area such that one average brightness is obtained for each of the first and second image areas of the first image data, wherein the second image area is other than the first image area among the first image data;
analyze, using an independent component analysis method, the average brightness of each of the first image area and the second image area of the first image data to obtain a first movement information, which contains a first intensity variation of signal noise caused by movement, and a first physiology information;
abandon all the first movement information to eliminate the signal noise caused by movement, without calculating the physiological characteristic according to the first movement information;
divide each of the second image data into a third image area of the second image data and a fourth image area of the second image data, respectively calculate an average brightness of each of the third image area and the fourth image area such that one average brightness is obtained for each of the third and fourth image areas of the second image data, wherein the fourth image area is other than the third image area among the second image data;
analyze, using the independent component analysis method, the average brightness of each of the third image area and the fourth image area of the second image data to obtain a second movement information, which contains a second intensity variation of the signal noise caused by movement, and a second physiology information;
abandon all the second movement information to eliminate the signal noise caused by movement, without calculating the physiological characteristic according to the second movement information;
calculate a physiological characteristic of the user according to the first physiology information and the second physiology information when the calculated displacement of the finger does not exceed a displacement threshold; and
not calculate the physiological characteristic according to the first image data and the second image data when the calculated displacement of the finger exceeds the displacement threshold; and
a response unit configured to respond to the displacement and the physiological characteristic.

* * * * *